United States Patent
Parthasaradhi Reddy et al.

(10) Patent No.: US 7,687,653 B2
(45) Date of Patent: Mar. 30, 2010

(54) PROCESS FOR THE PREPARATION OF LERCANIDIPINE

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Dandamudi Satish Kumar, Hyderabad (IN)

(73) Assignee: Hetero Drugs Limited, Hyderabad (IN)

( * ) Notice: Subject to any disclaimer, the term of this patent is extended or adjusted under 35 U.S.C. 154(b) by 236 days.

(21) Appl. No.: 11/570,533

(22) PCT Filed: Jun. 15, 2005

(86) PCT No.: PCT/IN2005/000198

§ 371 (c)(1),
(2), (4) Date: Dec. 13, 2006

(87) PCT Pub. No.: WO2006/134606

PCT Pub. Date: Dec. 21, 2006

(65) Prior Publication Data

US 2009/0227800 A1     Sep. 10, 2009

(51) Int. Cl.
*C07F 7/10*  (2006.01)

(52) U.S. Cl. .................................................... 556/413
(58) Field of Classification Search ................ 556/413
See application file for complete search history.

(56) References Cited

U.S. PATENT DOCUMENTS 4,705,797 A    11/1987   Nardi et al.

FOREIGN PATENT DOCUMENTS

| EP | 0060897 A1 | 10/1981 |
| WO | WO96/35666 A1 | 11/1996 |
| WO | WO96/35668 A1 | 11/1996 |

OTHER PUBLICATIONS

International Search Report and the Written Opinon of the International Searching Authority, or the Declaration Dated Mar. 8, 2006.

*Primary Examiner*—Elvis O Price
(74) *Attorney, Agent, or Firm*—Caesar, Rivise, Bernstein, Cohen & Pokotilow, Ltd.

(57) ABSTRACT

The invention provides a novel process for the preparation of lercanidipine or a pharmaceutical acceptable salt using novel intermediates. Thus, 2,N-dimethyl-N-(3,3-diphenylpropyl)-1-amino-2-propanol is reacted with trimethylsilyl chloride in presence of triethyl amine in methylene chloride to give 2,N-dimethyl-2-(trimethylsilyloxy)-N-(3,3-diphenylpropyl)-1-propanamine, which is then reacted with 2,6-dimethyl-5-methoxycarbonyl-4-(3-nitrophenyl)-1,4-dihydropyridine-3-carbonyl chloride for 2 hours and crystallized to obtain lercanidipine hydrochloride.

3 Claims, No Drawings

PROCESS FOR THE PREPARATION OF LERCANIDIPINE

FIELD OF THE INVENTION

The present invention provides a novel process for the preparation of high purity lercanidipine and pharmaceutically acceptable acid addition salts of lercanidipine; and solvates and hydrates thereof, in lesser reaction time with improved yield.

BACKGROUND OF THE INVENTION

U.S. Pat. No. 4,705,797 incorporated by reference herein discloses novel asymmetric diesters of 1,4-dihydro-2,6-dimethyl-pyridine-3,5-dicarboxylic acid, stereochemically isomeric forms and pharmaceutically acceptable salts thereof. These compounds are antihypertensive agents. Among them lercanidipine, chemically 1,4-dihydro-2,6-dimethyl-4-(3-nitrophenyl)-3,5-pyridinedicarboxylic acid 2-[(3,3-diphenylpropyl)methylamino]-1,1-dimethylethyl methyl ester is an antagonist of type-L calcium channels, and has been found to be very active as an antihypertensive and as an agent for the treatment of angina and coronary disease. Lercanidipine is represented by the following structure:

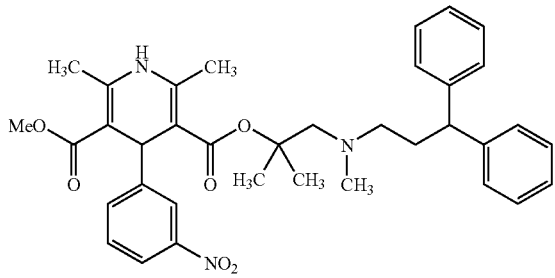

Processes for the preparations of Lercanidipine and related compounds were disclosed in U.S. Pat. No. 4,705,797 and WO 96/35668 A1 incorporated by reference herein.

According to U.S. Pat. No. 4,705,797, 2,N-dimethyl-N-(3,3-diphenylpropyl)-1-amino-2-propanol is esterified with diketene to form 1,1,N-trimethyl-N-(3,3-diphenylpropyl)-2-amino-2-propanol, which is then coupled with 3-nitrobenzaldehyde to give 1,1, N-trimethyl-N-(3,3-diphenylpropyl)-2-aminoethyl α-acetyl-3-nitrocinnamate, followed by cyclization with methy 3-aminocrotonate in refluxing isopropanol to give lercanidipine hydrochloride hemihydrate. The yield of lercanidipine obtained according to the process described in U.S. Pat. No. 4,705,797 is poor and the process involves column chromatographic purifications. Methods involving column chromatographic purifications cannot be used for large-scale operations, thereby making the process commercially not viable.

According to WO 96/35668, 2,6-dimethyl-5-methoxycarbonyl-4-(3-nitrophenyl)-1,4-dihydropyridine-3-carboxylic acid is halogenated with a halogenating agent in an aprotic solvent, followed by treatment with 2,N-dimethyl-N-(3,3-diphenylpropyl)-1-amino-2-propanol in an aprotic solvent and isolating the resultant lercanidipine as its anhydrous hydrochloride. This process involves direct condensation of 2, N-dimethyl-N-(3,3-diphenylpropyl)-1-amino-2-propanol with 2,6-dimethyl-5-methoxycarbonyl-4-(3-nitrophenyl)-1,4-dihydro-pyridine-3-carbonyl chloride.

The reaction requires longer time to complete and the yield obtained is not satisfactory.

The present invention is an improved, commercially viable process solving the aforesaid problems associated with processes described in the prior art.

The object of the present invention is to provide a process for preparing lercanidipine and pharmaceutically acceptable acid addition salts of lercanidipine, and solvates and hydrates thereof in high purity and in high yield using novel intermediates in lesser reaction time.

SUMMARY OF THE INVENTION

According to the present invention, there is provided an improved process for preparing lercanidipine of the formula I:

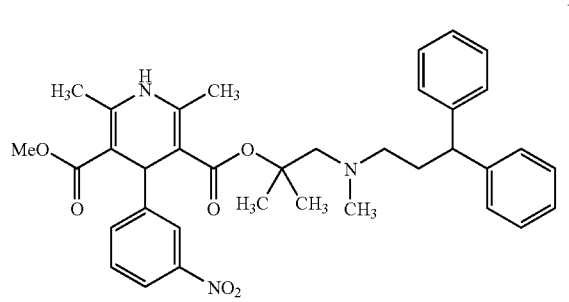

or a pharmaceutically acceptable salt thereof:

which comprises:

a) reacting the alcohol of the formula II:

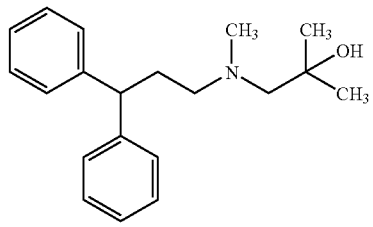

with a silyl compound of the formula III:

$$R_3SiX \qquad III$$

wherein R is independently alkyl, and X is Cl or Br in an aprotic solvent to give a silylated alcohol of formula IV:

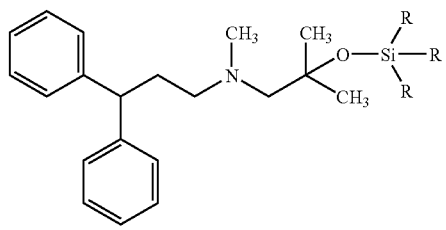

wherein R is as defined above;

b) reacting the silylated alcohol of the formula IV with the acid chloride of the formula V:

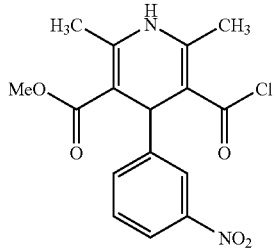

to give lercanidipine of the formula I and optionally convert the lercanidipine formed into a pharmaceutically acceptable acid addition salt.

Silyl compounds of the formula IV are novel and form part of the invention.

DETAILED DESCRIPTION OF THE INVENTION

According to the present invention, there is provided an improved process for preparing lercanidipine of the formula I:

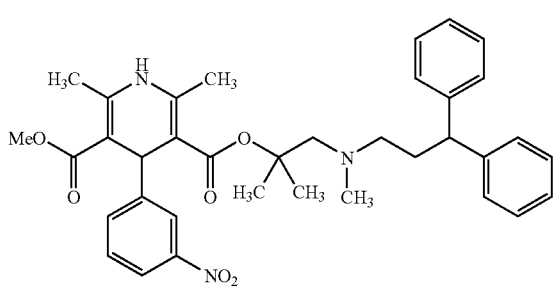

or a pharmaceutically acceptable salt thereof;
which comprises:
a) reacting the alcohol of the formula II:

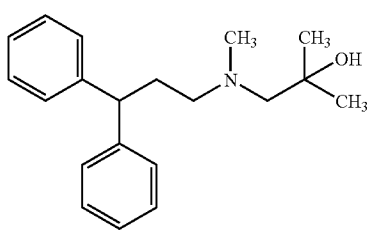

with a silyl compound of the formula III:

$R_3SiX$  III wherein R is independently alkyl, and X is Cl or Br in an aprotic solvent to give a silylated alcohol of the formula IV:

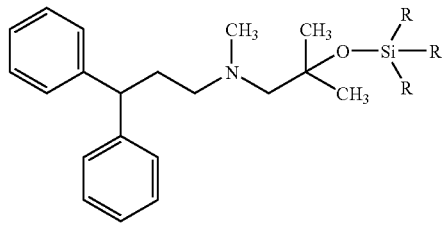

wherein R is as defined above;
b) reacting the silylated alcohol of the formula IV with the acid chloride of the formula V:

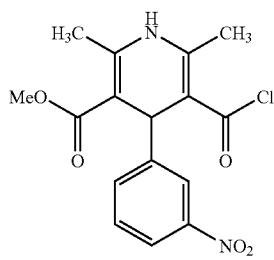

to give lercanidipine of the formula I and optionally converting the lercanidipine formed into a pharmaceutically acceptable acid addition salt.

Preferably R is independently methyl or ethyl, and more preferably, R is methyl.

The aprotic solvent is preferably selected from chlorinated solvents such as methylene chloride, ethylene chloride and chloroform; and hydrocarbon solvents such as n-hexane, n-heptane and cyclohexane. The more preferable solvent is methylene chloride or n-heptane.

The reaction in step (a) is carried out in the presence of an organic base, preferably amines such as triethyl amine, trimethyl amine or N,N-diisopropylethyl amine, and more preferably triethyl amine.

The reaction is preferably carried out at $-10°$ C. to $0°$ C., more preferably at $-5°$ C. to $0°$ C.

The silylation is normally completed in less than 5 hours, usually 1 hour 30 minutes to 3 hours.

The silyl compound of the formula IV are novel and forms part of the invention.

The compounds of formula IV wherein R is independently methyl or ethyl are preferable. The compound of formula IV, wherein R is methyl is more preferable.

The reaction (step b) of the silyl compound of the formula IV with the acid chloride of formula V is normally completed in less than 5 hours, usually 1 hour 30 minutes to 3 hours.

The reaction medium of step (a) containing the silyl compound may preferably directly be used, or the silyl compound may be isolated from the reaction medium for example by distilling off the solvent and then used in the step (b).

The reaction medium obtained by converting the corresponding carboxylic acid of the formula V to the acid chloride by known processes may be used as a source of the acid chloride of the formula V. The reaction is preferably carried out at 0-80° C. and more preferably at 0-40° C.

The reaction is normally completed within 4 hours, usually within 2 hours.

After the reaction is completed, the reaction mass is washed with water to remove by-products and salts, crystallized from a suitable solvent or a mixture of solvents by conventional means.

Preferably aprotic solvents are used in step (b). The preferable aprotic solvent is selected from chlorinated solvents such as methylene chloride, ethylene chloride, and hydrocarbon solvents such as n-hexane, n-heptane and cyclohexane. the more preferable solvent is methylene chloride or n-heptane.

If not otherwise defined herein, alkyl includes lower alkyl such as ($C_1$-$C_4$)-alkyl, preferably methyl or ethyl.

Lercanidipine and pharmaceutically acceptable salts of lercanidipine of the present invention also include their solvates and hydrates.

Preferable pharmaceutically acceptable acid addition salts of the formula I, are, but are not limited to, the salts of lercanidipine obtained from hydrochloric acid, hydrobromic acid, hydroiodic acid, methanesulfonic acid and benzenesulfonic acid; the more preferable salt being lercanidipine hydrochloride.

The invention will now be further described by the following examples, which are illustrative rather than limiting.

EXAMPLE

Step-I 2,6-Dimethyl-5-methoxycarbonyl-4-(3-nitrophenyl)-1,4-dihydroyridine-3-carboxylic acid (6.5 gm) is suspended in methylene chloride (39 ml), N,N'-dimethylformamide (7.5 ml) is added and then cooled to −10° C. under $N_2$ atmosphere. Thionyl chloride (3.5 gm) is slowly added to the reaction mass at 10° C. to −5° C. and maintained for 1 hour at the same temperature to obtain 2,6-dimethyl-5-methoxycarbonyl-4-(3-nitrophenyl)-1,4-dihydropyridine-3-carbonyl chloride as a clear solution.

Step-II

2,N-Dimethyl-N-(3,3-diphenylpropyl)-1-amino-2-propanol (5.0 gm) is dissolved in methylene chloride (25 ml) at 25-30° C., triethylamine (2.5 gm) is added and then the contents are cooled to 10-15° C. under $N_2$ atmosphere. Trimethylsilyl chloride (2.5 gm) is slowly added to the reaction mass while maintaining the temperature 10-15° C., the mass temperature is raised to 25-30° C. and maintained for 2 hours at the same temperature to give the reaction mass of 2,N-dimethyl-2-(trimethylsilyloxy)-N-(3,3-diphenylpropyl)-1-propanamine.

Step-III

The reaction mass of 2, N-dimethyl-2-(trimethylsilyloxy)-N-(3,3-diphenylpropyl)-1-propanamine, obtained in step-II, is slowly added to 2,6-dimethyl-5-methoxycarbonyl-4-(3-nitrophenyl)-1,4-dihydropyridine-3-carbonyl chloride solution obtained in step-I at −10° C. to 0° C. The mass temperature is slowly raised to 25-30° C., and stirred for 2 hours at the same temperature. Then the reaction mass is cooled to 5-10° C., water (30 ml) is added and stirred for 15 minutes. The resulting organic layer is washed with 20% W/W aqueous sodium chloride solution, dried over sodium sulfate and concentrated the organic layer under vacuum. The organic layer is striped off with ethyl acetate, ethyl acetate (80 ml) is added, seeded with pure Lercanidipine hydrochloride and stirred for 20 hours at 25-30° C. The solid is filtered and slurried with ethyl acetate, filtered and the solid is washed with ethyl acetate. The resulting solid is purified in an ethyl alcohol/ethyl acetate mixture to give 11 gm of 99.5% pure lercanidipine hydrochloride.

Without further elaboration of the foregoing will so fully illustrate our invention that others may, by applying current or future knowledge, adapt the same for use under various conditions of service.

We claim:

1. Compound of the formula IV:

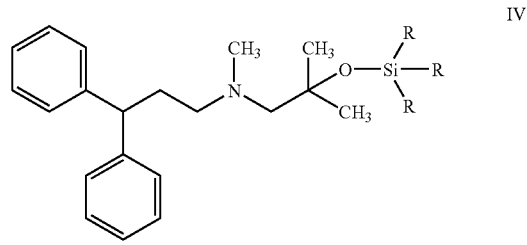

wherein R is alkyl.

2. The compound of claim 1 wherein R is independently methyl or ethyl.

3. The compound of claim 2 wherein R is methyl.

* * * * *